(12) United States Patent
Warburton

(10) Patent No.: US 6,887,218 B2
(45) Date of Patent: May 3, 2005

(54) FLEXIBLE INSERT FOR APPLICATION ONTO A RIGID BREASTSHIELD

(76) Inventor: Stephen R. Warburton, 12643 S. Bridge Creek Way, Draper, UT (US) 84020

( * ) Notice: Subject to any disclaimer, the term of this patent is extended or adjusted under 35 U.S.C. 154(b) by 0 days.

(21) Appl. No.: 10/385,303

(22) Filed: Mar. 10, 2003

(65) Prior Publication Data
US 2004/0181187 A1 Sep. 16, 2004

(51) Int. Cl.$^7$ ................................................ A61M 1/06
(52) U.S. Cl. ........................................................ 604/74
(58) Field of Search ............................ 604/73–76, 132, 604/133; D24/109

(56) References Cited

U.S. PATENT DOCUMENTS

| | | | | |
|---|---|---|---|---|
| 5,100,406 A | * | 3/1992 | Panchula | 604/74 |
| 5,885,246 A | * | 3/1999 | Ford | 604/74 |
| 6,273,868 B1 | * | 8/2001 | Nordvik | 604/74 |
| D456,897 S | * | 5/2002 | Atkin et al. | D24/109 |
| 6,579,258 B1 | * | 6/2003 | Atkin et al. | 604/74 |
| 6,673,037 B1 | * | 1/2004 | Silver | 604/74 |

* cited by examiner

Primary Examiner—Sharon Kennedy
(74) Attorney, Agent, or Firm—Kirton & McConkie; Michael F. Krieger

(57) ABSTRACT

A flexible insert that is easily applied to a generally rigid breastshield, fits a variety of varying nipple and breast sizes, and that compresses the breast tissue and nipple in a manner akin to an infant's suckling during breastfeeding is provided.

8 Claims, 4 Drawing Sheets

FLEXIBLE INSERT FOR APPLICATION ONTO A RIGID BREASTSHIELD

BACKGROUND OF THE INVENTION

1. Field of the Invention

The present invention relates generally to breastshields, and more particularly, to a flexible insert that can be easily applied to rigid breastshields to enhance breast milk expression.

2. Background and Related Art

As the most scientifically proven beneficial form for feeding infants in the world today, breastfeeding is prevalent and continues to grow in popularity. Scientists continually discover the manifold advantages of breastfeeding. Breast milk is touted as perfectly balanced for babies, providing just the right ratios of necessary nutrients. Additionally, breast milk changes composition throughout each breastfeeding session, throughout the day, and even throughout the year to suit the individual and growing needs of infants (Renfrew, M. *The New Bestfeeding: Getting Breastfeeding Right for You*, Pg. 5, CelestialArts 2000) Breast milk is the primary protection for infants against infection and disease, and studies even suggest breast milk contributes to higher IQ's and optimal brain development. Breastfeeding is also more practical. On average it can cost $20–$40 a week for formula, which is the only safe alternative to breastfeeding. In contrast, breast milk is free and available without preparation. Thus, women and their babies worldwide are enjoying the benefits of breastfeeding.

A woman who returns to the workplace while breastfeeding, or even a woman who needs to express milk in addition to breastfeeding (perhaps in the instance where she is painfully engorged), might use a breast pump for expression of milk. Breast pumps are popular because they enable women to maintain their milk supply while being away or relieve painfully swollen breasts. Breast pumps generally consist of a vacuum source, a receptacle where the expressed milk is held, and a funnel, essentially a cone ending in a tube, connected to the receptacle and the vacuum, which receives the breast and nipple. Upon activation of the vacuum, the negative pressure and funnel work together to stimulate the breast. Milk then begins to "letdown," or become expressed, and runs into the nipple tunnel and down the receptacle where it can be stored for later use.

Unfortunately, using breast pumps can be unfavorable. Women most often complain about the breast pump's funnel (hereinafter referred to as the "breastshield") and its rigidity, shape and generalized form, which are usually not at all similar to a baby's mouth. Hence, many women find using breast pumps uncomfortable and more difficult.

One of the more painful conditions associated with breastfeeding and breast pumping occurs when a woman's nipples become cracked and sore. Sore and cracked nipples occur when not enough of the breast tissue surrounding the nipple is taken into the baby's mouth when nursing. Babies need to nurse from the breasts, and not just the nipples. When a baby compresses his or her gum line in the appropriate area surrounding the woman's breast and nipple, milk expression is optimal and painless.

The same soreness and cracking can also result from nipple damage caused by breast pumps. Pain occurs because during breast pump use, though the breast is initially pulled forward into the breastshield at the onset of negative pressure, after that, only the nipple moves back and forth relative to the breastshield's tubular extension. This motion, which makes primarily only the nipple to move back and forth within the rigid shield, may create friction between the nipple and area between the cone and tubular extension of the breastshield. Such friction results in nipple cracking and soreness. Also, the rigidity and generalized form of the shield is so dissimilar to a baby's mouth that letdown is much more difficult. Breast pumps are also less optimal for milk expression because the breastshields available today do not closely mimic the compression of the baby's gum line over the milk sinuses and the tongue's stripping action.

Numerous additional shortcomings with current breastshields are also present. Specifically, there is a need for a flexible breastshield that can compress the breast tissue and nipple similarly to a baby's gum line, and also has the ability to pull the breast back and forth relative to the rigid shield, which creates optimal massage and fosters successful, painless milk expression. There is also a need in the industry for a flexible shield that can be easily applied over any universal rigid shield. Moreover, there is a need for a breastshield that is not only more easily applied onto a more rigid shield, but also can, upon onset of the vacuum, easily pull the breast into the shield without having to take great care in centering the nipple within the shield. Moreover, there is a need for a breastshield, which by nature of its flexible material, can be used by a variety of women with different breast and nipple sizes, and especially by those women who do not fit the generalized rigid shield manufactured to fit average size nipples and breasts. Finally, there is a need for a breastshield that allows much of the breast to remain exposed, enabling the woman to manually massage her breast, which is often necessary to relieve painful engorgement or to work out a plugged duct.

SUMMARY AND OBJECTS OF THE INVENTION

Some embodiments of the present invention provide a flexible insert that is easily applied to a generally rigid breastshield, fits a variety of varying nipple and breast sizes, and that compresses the breast tissue and nipple in a manner akin to an infant's suckling during breastfeeding.

In a preferred embodiment, the flexible insert can be applied to the average rigid breastshield (hereinafter "rigid shield"). The flexible insert is taut over the rigid shield and thus, great care in centering the nipple over the shield is unnecessary. In fact, placing the breast and nipple into most available shields requires precision, and misplacement can result in pain. Moreover, upon activation of the vacuum, the breast and nipple are immediately drawn into the flexible insert so that comfort and initial breast pumping are optimal. The flexible material is able to conform or expand to different size breasts and nipples. Moreover, because the flexible material moves relative to the rigid shield, the breast can either fill the entire rigid shield space, or remain within the flexible insert, and thereby accommodate all sizes of women. This relative movement of the flexible insert to the rigid shield also fosters enhanced milk expression.

In this preferred embodiment, the flexible insert is made of soft or flexible material and generally comprises a conical portion having two surfaces: a breast-receiving surface where the breast and nipple are received, and a shield-contacting surface that in certain areas, either aligns or comes close to aligning the inner surface of the rigid shield. The flexible insert can generally be described as having a wide-diameter end and a small-diameter end. Attached to the small-diameter end is a tubular extension that is integrally connected to the conical portion. During pumping, the nipple will primarily reside within this tubular extension. The rigid shield described herein is common in the breast pump industry and need not be exactly rigid, just more rigid than the flexible insert so application thereon is feasible.

In this preferred embodiment, the flexible insert closely parallels the shape of universal rigid breastshields, yet overcomes deficiencies of rigid shields and available flexible shields. Rigid shields are usually shaped similarly to funnels with a wide-diameter conical area and a small-diameter tubular area extending from the conical area. In this preferred embodiment, upon activation of the pump, a vacuum is created within the rigid shield and flexible insert. The vacuum then draws the nipple and breast further into the flexible insert. More specifically, the breast is drawn into the conical portion while the nipple is drawn into the tubular extension. Unlike the prior art, the flexible insert moves relative to the rigid shield. Also unlike the prior art, the breast tissue and nipple, simultaneously, move back and forth within the rigid shield.

Moreover, in this preferred embodiment nodules are intermittently spaced around the conical portion of the flexible insert. They are integrally formed with the flexible insert and protrude from both the breast-receiving surface and shield-contacting surface. The pressure during vacuum causes the shield-contacting surface of the flexible insert to try and align with the inner surface of the shield. However, these protruding nodules prevent complete alignment and in a way, act as a stop to prevent complete alignment.

However, the protruding nodules extending from the breast-receiving surface also create a compression action akin to a baby's gum line. As a reaction to the breast pump's vacuum, the space between the nodules continues to be drawn inward toward the inner surface of the rigid shield, attempting to, and in instances, making contact with the rigid shield. This creates compression akin to a baby's suckling because the backside of the nodules (i.e. the rigid shield contacting side) first presses against the inner surface of the shield during vacuum. This pressure from the nodules pressing against the inner surface of the rigid shield then translates onto the other side of the nodules (i.e., the breast-receiving side) causing compression of the nodules into the breast much like a baby's gum line. Put another way, the intermittent pressure from the vacuum makes the nodules' compression into the breast tissue surrounding the nipple a kneading-like motion, similar to a baby's suckling. Furthermore because the flexible insert, with the breast and nipple contained therein, actually moves back and forth relative to the rigid flexible insert, and not just the nipple, this is much gentler on the breast and milk express is optimal.

In some embodiments, the nodules are not necessarily circular, but rather can be characterized as protrusions that vary in shape or form.

In other embodiments, the flexible insert can be integrally connected to the rigid shield in manufacturing.

In other embodiments, the flexible insert can have a flange integrally connected to the wide-diameter end perimeter of the conical portion so that it can tightly fit over the rigid shield.

In other embodiments, the tubular extension of the flexible insert is sufficiently long so that it extends well into the tubular portion of the rigid insert and no milk is able to escape and retract up into the conical area of the rigid shield.

Accordingly, it is an object of some embodiments of the present invention to provide a flexible insert for breastshields, which upon activation of the breast pump, reacts in a motion closely mimicking the compression of the baby's gum line over the milk sinuses.

Another object of some embodiments of the present invention is to provide a flexible insert that pulls the breast and nipple, simultaneously, back and forth relative to the rigid shield to create optimal massage and foster successful, painless milk expression.

Yet another object of some embodiments of the present invention is to provide a flexible insert that can be easily applied over any universal rigid shield.

A further object of some embodiments of the present invention to provide an insert that is not only more easily applied onto a more rigid shield, but also can, upon onset of the vacuum, easily pull the breast into the shield without having to take great care in centering the nipple within the shield.

Another object of some embodiments of the present invention provide a flexible insert for a breast shield, which by nature of its flexible material, can be used by a variety of women with different breast and nipple sizes, and especially by those women who do not fit the generalized rigid shield manufactured to fit average size nipples and breasts.

A final object of some embodiments of the present invention is to provide a flexible insert for application into a rigid breastshield that allows much of the breast to remain exposed, thereby enabling the woman to manually massage her breast, which is often necessary to relieve painful engorgement or plugged ducts.

These and other objects of the present invention will become more fully apparent from the following description, drawings, and claims. Other objects will likewise become apparent from the practice of the invention as set forth hereafter.

BRIEF DESCRIPTION OF THE DRAWINGS

The foregoing and other objects and features of the present invention will become more fully apparent from the accompanying drawings when considered in conjunction with the following description and appended claims. Although the drawings depict only typical embodiments of the invention and are thus, not to be deemed limiting of the invention's scope, the accompanying drawings help explain the invention in added detail.

DETAILED DESCRIPTION OF THE INVENTION

It is emphasized that the present invention, as illustrated in the figures and description herein, can be embodied in other forms. Thus, neither the drawings nor the following more detailed description of the various embodiments of the system and method of the present invention limit the scope of the invention. The drawings and detailed description are merely representative of the particular embodiments of the invention; the substantive scope of the present invention is limited only by the appended claims. The various embodiments of the invention will best be understood by reference to the drawings, wherein like elements are designated by like alphanumeric characters throughout.

Figure 1:
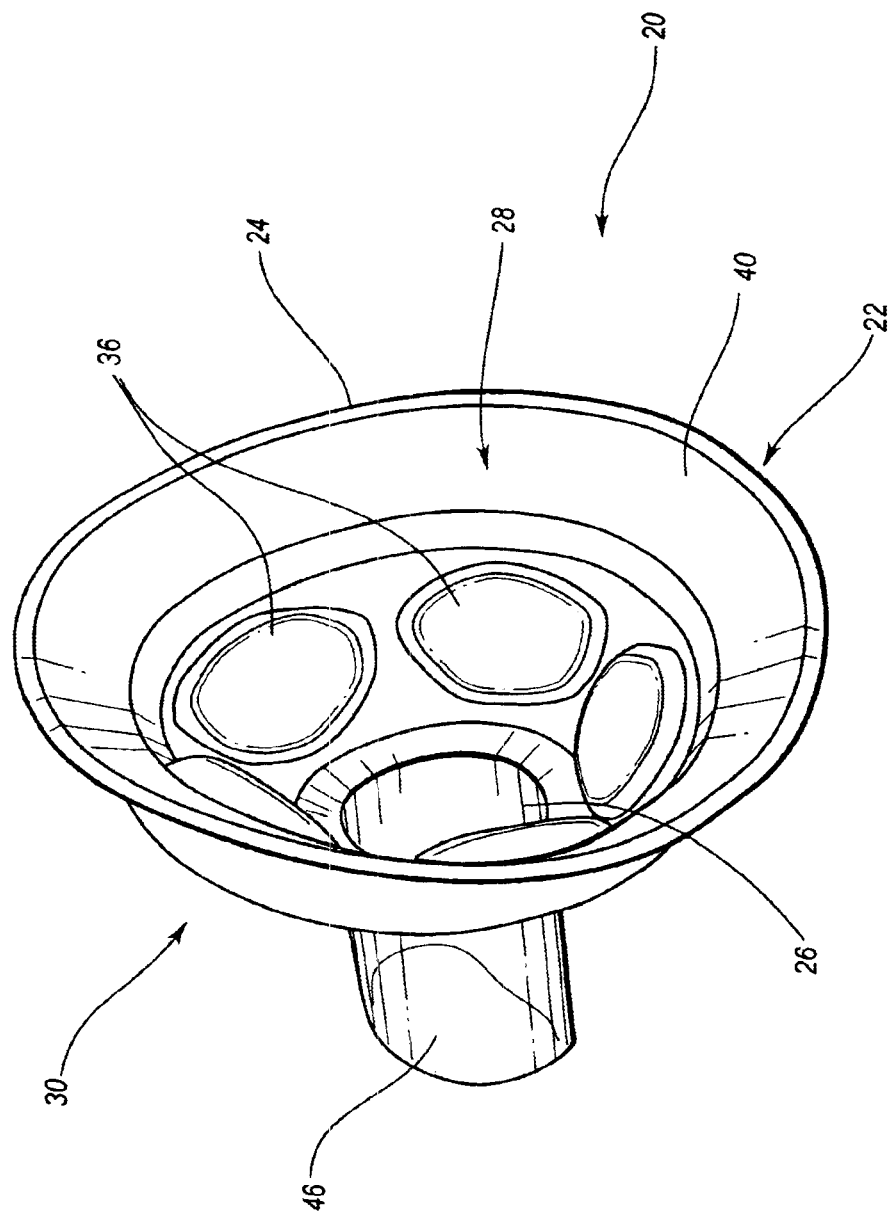
FIG. 1 depicts one perspective of the flexible insert showing: the conical portion along with the breast-receiving surface; the protruding nodules extending therefrom; and the flange that is integrally connected with the conical portion that is used to connect to the rigid shield.
Figure 2:
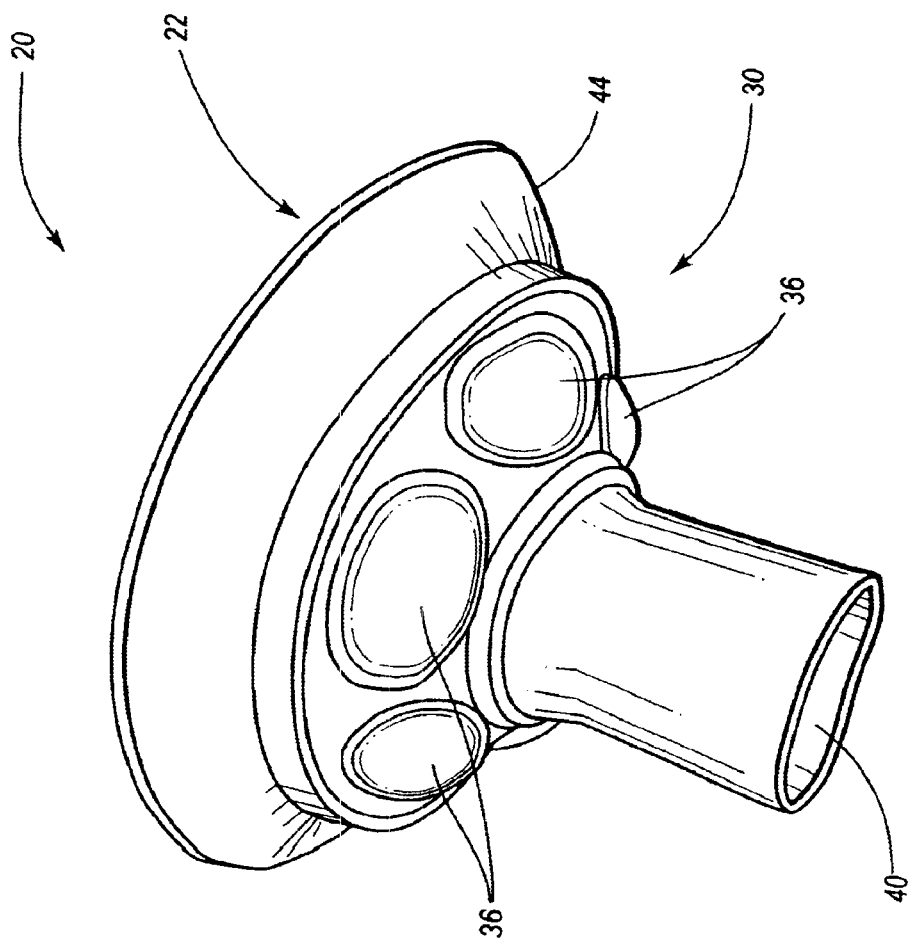
FIG. 2 depicts another perspective of the flexible insert showing: again the conical portion; the rigid-shield contacting surface; the protruding nodules extending therefrom; the flange aligning the wide-diameter end of the conical portion and the tubular extension integrally connected with the small-diameter end of the conical portion.
Figure 4A:
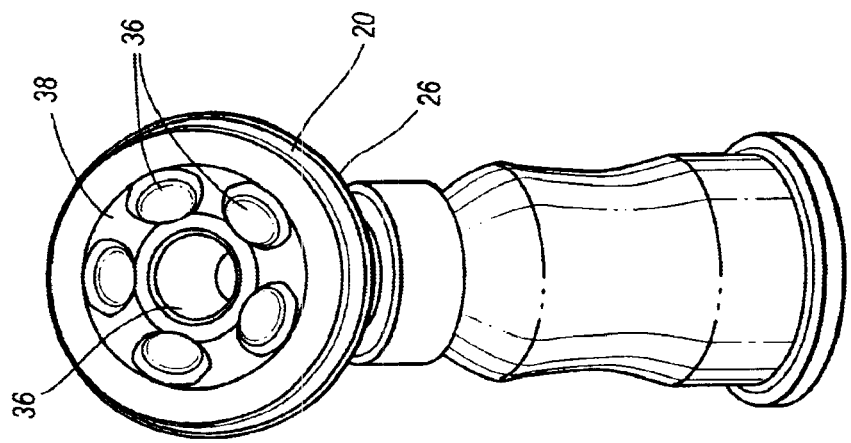
FIG. 4a is another view of the flexible insert applied onto a rigid shield, this time exposing the breast-receiving surface and showing how such surface is taut, almost flat, with respect to the rigid shield's conical area, prior to the vacuum.
Figure 4:
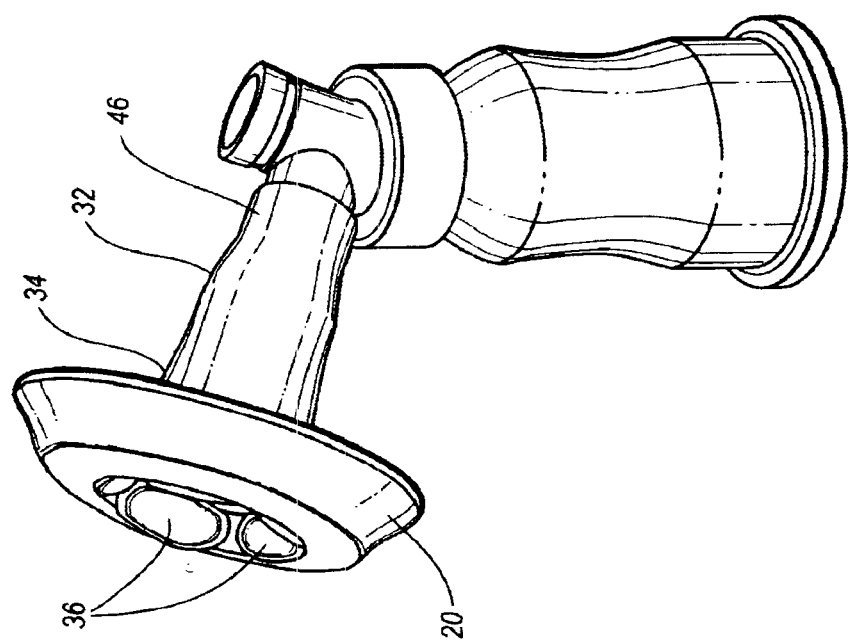
FIG. 4 depicts the flexible insert applied onto one example of a rigid shield. The rigid shield is also connected to the milk receptacle common in breast pumps.

With reference now to the accompanying drawings, FIGS. 1, 2 and 4 depict varying perspectives of the preferred embodiment of a flexible insert 20. In a preferred embodiment, the flexible insert 20 comprises a conical portion 22 that has a wide-diameter end 24 and a small-diameter end 26. The conical portion 22 also has two sides (28, 30). One side is a breast-receiving surface 28 (more clearly displayed in FIG. 1) that will receive and encompass the breast during a breast pump's operation. The opposite side of the breast-receiving surface 28 is a shield-contacting surface 30 (more clearly depicted in FIG. 2) that aligns itself with the inner surface of a universal rigid breastshield's 32 (FIG. 4) conical area 34 (FIG. 4) when the vacuum has drawn the flexible insert 20 in due to the vacuum's negative pressure. Integrally connected within the conical portion 22 are nodules 36, which by nature of their integration within the conical portion 22, protrude from both the breast-receiving surface 28 and shield-contacting surface 30.

The essential elements enabling the flexible insert 20 to behave similarly to a baby's gumline are also clearly depicted in FIGS. 1, 2 and 4. In this preferred embodiment, the nodules 36 are intermittently spaced around the conical portion 22, such that there are spaces 38 between each of the nodules 36 consisting of the conical portion's 22 material. Furthermore, a tubular extension 40 extends from the small-diameter end 26 of the conical portion 22. The nipple will primarily reside within this tubular extension 40. Extending from the opposite end of both the small-diameter end 26 and the tubular extension 40, is a flange 42 that connectedly extends around the perimeter of the wide-diameter end 24 of the conical portion 22. This flange 42 folds over the rigid shield's 32 opening at the wide end of the conical area 34, which without the flexible insert 20, would normally receive the breast. The flange 42 has a lip 44 (FIG. 2) that fits over the perimeter of the rigid shield 32 when the flange 42 of the conical portion 22 is taut, thereby creating an interference fit against the perimeter of the rigid shield 32.

The flexible insert 20 enables optimal milk expression as follows: in the preferred embodiments depicted in FIGS. 1, 2 and 4, it is understood that once the flexible insert 20 is attached to the rigid shield 32, the breast pump can be activated creating a vacuum within the rigid shield 32. The vacuum creates negative pressure causing the flexible insert 20 to be pulled inwardly toward the tubular portion of a rigid shield 46. The vacuum initially draws the nipple and breast further into the flexible insert 20. The breast is drawn into the conical portion 22 while the nipple is drawn into the tubular extension 40. After the vacuum creates intermittent spurts of negative pressure, unlike the prior art, the flexible insert 20 moves relative to the rigid shield 32. It only aligns with the inner conical area 34 of the rigid shield 32 in localized regions, and never completely. Also, unlike the prior art, the breast tissue and nipple, simultaneously, move back and forth within the flexible insert 20 and relative to the rigid shield 32.

In sum, due to the vacuum, the shield-contacting surface 30 of the conical portion 22 has a tendency to align itself with the inner surface of the rigid shield 32. However, the nodules 36 protruding from the shield-contacting surface 30 act as a type of detent for the rigid-shield contacting surface 30 from becoming completely aligned with the conical area 34 of the rigid shield 32. While the nodules 36 stop the flexible insert 20 from becoming completely aligned within the conical area 34 of the rigid shield 32, the spaces 38 between the nodules continue to press against, or try to press against, the conical area 34 of the rigid shield 32 until the conical portion 22 of the flexible insert 20 either contacts or comes close to contact with the rigid shield 32. This creates compression akin to a baby's suckling because the backside of the nodules 36 (i.e. the shield-contacting surface 30) press against the inner conical area 34 of the rigid shield 32 during vacuum. The pressure from the nodules 36 pressing against the inner conical area 34 of the rigid shield 32 then translates onto the other side of the nodules 36 (i.e., the breast-receiving surface 28) causing compression of the nodules into the breast tissue, over the milk sinuses much like a baby's gum line. The intermittent pressure from the vacuum makes the nodules 36 compression into the breast tissue surrounding the nipple a kneading-like motion, akin to a baby's gum line and suckling.

Figure 3:
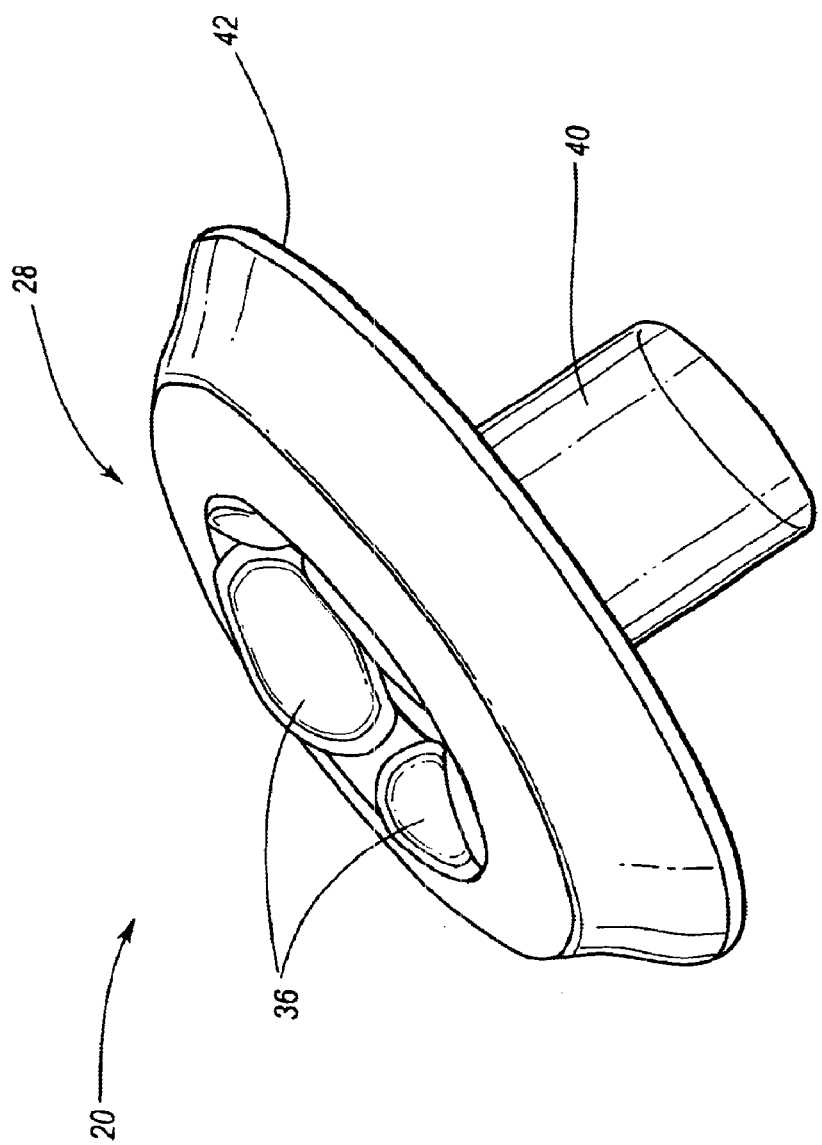
FIG. 3 depicts yet another perspective of the flexible insert, this time with the flange bent over in the form that it would take once tightly fit onto the rigid shield.

FIG. 3 depicts the flexible insert 20 with the flange 42 folded over, as it would appear once applied to rigid shield 32.

FIGS. 4 and 4a demonstrate how the flexible insert 20 is taut over the rigid shield 32 and thus, great care in centering the nipple over the shield is unnecessary. FIG. 4 also shows the rigid shield 32 applied to a milk receptacle storage unit which are common units in the breastpump industry.

What is claimed is:

1. A flexible insert for a rigid breastshield comprising:
   a conical portion for receiving a breast therein having a wide-diameter end, a small-diameter end, a breast-receiving surface, and a shield-contacting surface;
   a tubular extension that extends from said small-diameter end of said conical portion for receiving a nipple therein;
   a flange integrally formed with said conical portion that encircles said wide-diameter end of said conical portion and;
   nodules integrally formed with said conical portion that are intermittently spaced around said conical portion, wherein each said nodule protrudes from both said breast-receiving surface and said shield-contacting surface.

2. A flexible insert as in claim 1, wherein said flexible insert is comprised of silicone polymer.

3. A flexible insert as in claim 1, wherein said nodules are oval-shaped.

4. A flexible insert as in claim 1, wherein said nodules are comprised of solid silicone polymer.

5. A flexible insert as in claim 1, wherein said flexible insert is adapted to move back and forth within and relative to said rigid shield.

6. A flexible insert as in claim 1, wherein said flange is integrally connected to said rigid shield.

7. A flexible insert as in claim 1, wherein said flange further comprises a lip that connects said flange to said rigid shield.

8. An improved breastpump system, comprising:

a receptacle for collecting breast milk;

a substantially rigid breastshield removably attached to said receptacle;

vacuum generating means coupled to said breastshield for selectively intermittently generating negative pressure within said breastshield; and a substantially flexible breastshield insert coupled to an outer rim of said breastshield, said substantially flexible breastshield insert comprising:

a conical portion for receiving a breast therein, having a wide-diameter end, a small-diameter end, a breast-receiving surface, and a shield-contacting surface;

a tubular extension extending from said small-diameter end for receiving a nipple therein;

at least one flange integrally formed with said conical portion, wherein said at least one flange extends from said wide-diameter end of said conical portion; and nodules integrally formed with said conical portion, said nodules intermittently spaced around said conical portion, wherein each said nodule protrudes from both said breast-receiving surface and said shield-contacting surface.

\* \* \* \* \*